US006633392B1

(12) United States Patent
Singh et al.

(10) Patent No.: US 6,633,392 B1
(45) Date of Patent: Oct. 14, 2003

(54) X-RAY REFLECTANCE SYSTEM TO DETERMINE SUITABILITY OF SION ARC LAYER

(75) Inventors: Bhanwar Singh, Morgan Hill, CA (US); Arvind Halliyal, Sunnyvale, CA (US); Ramkumar Subramanian, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/052,142

(22) Filed: Jan. 17, 2002

(51) Int. Cl.$^7$ .............................................. G01B 11/28
(52) U.S. Cl. ...................................... 356/630; 356/503
(58) Field of Search ........................... 438/14; 356/381, 356/630; 524/434; 430/270.1

(56) References Cited

U.S. PATENT DOCUMENTS

| | | | |
|---|---|---|---|
| 5,600,165 A | 2/1997 | Tsukamoto et al. | 257/323 |
| 5,705,430 A | 1/1998 | Avanzino et al. | 437/195 |
| 5,710,067 A | 1/1998 | Foote et al. | 437/238 |
| 5,821,168 A | 10/1998 | Jain | 438/692 |
| 5,956,587 A | 9/1999 | Chen et al. | 438/255 |
| 5,968,324 A | 10/1999 | Cheung et al. | 204/192.28 |
| 6,008,120 A | 12/1999 | Lee | 438/634 |
| 6,040,619 A | 3/2000 | Wang et al. | 257/649 |
| 6,041,098 A | 3/2000 | Touryanski et al. | 378/70 |
| 6,103,456 A | 8/2000 | Tobben et al. | 430/317 |
| 6,114,233 A | 9/2000 | Yeh | 438/622 |
| 6,121,098 A | 9/2000 | Strobl | 438/301 |
| 6,140,224 A | 10/2000 | Lin | 438/634 |
| 6,184,073 B1 | 2/2001 | Lage et al. | 438/238 |
| 6,187,663 B1 | 2/2001 | Yu et al. | 438/624 |
| 6,211,068 B1 | 4/2001 | Huang | 438/634 |
| 6,228,760 B1 | 5/2001 | Yu et al. | 438/636 |
| 6,232,386 B1 * | 5/2001 | Vargo | 524/434 |
| 6,261,949 B1 | 7/2001 | Sukekawa | 438/637 |
| 6,265,296 B1 | 7/2001 | Yen et al. | 438/586 |
| 6,268,287 B1 | 7/2001 | Young et al. | 438/671 |
| 6,365,320 B1 * | 4/2002 | Foote | 430/270.1 |
| 6,392,749 B1 * | 5/2002 | Meeks | 356/381 |

FOREIGN PATENT DOCUMENTS

JP  955351  2/1997  ..................... 21/27

OTHER PUBLICATIONS

Materlik, Gerhard Dr., "X–Ray Investigations on Thin Films, Adsorbate Systems and Growth Phenomena," HASY-LAB Research Group, http://www–hasylab.desy.de/science/groups/materlik_group/xsw/xsw.html.

Stoev, Krassimir and Sakurai, Kenji, "Recent Theoretical Models in Grazing Incidence X–Ray Reflectometry," The Rigaku Journal, vol. 14, No. 2 1997, pp. 22–37.

* cited by examiner

Primary Examiner—John F. Niebling
Assistant Examiner—Andre C Stevenson
(74) Attorney, Agent, or Firm—Amin & Turocy, LLP

(57) ABSTRACT

One aspect of the present invention relates to a method to facilitate formation of an oxide portion of an anti-reflective layer on a substrate. The method involves the steps of forming an oxidized portion of an anti-reflective coating over an anti-reflective layer disposed on the substrate; reflecting a beam of x-ray radiation at the oxidized portion; generating a measurement signal based on the reflected portion of the light beam; and determining a thickness of the oxidized portion based on the measurement signal while the oxidized portion is being formed at the substrate.

19 Claims, 7 Drawing Sheets

X-RAY REFLECTANCE SYSTEM TO DETERMINE SUITABILITY OF SION ARC LAYER

TECHNICAL FIELD

The present invention generally relates to monitoring and controlling semiconductor processing. In particular, the present invention relates to a system and method for optimizing oxidation of an antireflective coating layer via a x-ray reflectometry system.

BACKGROUND ART

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required. This may include the width and spacing of interconnecting lines, spacing and diameter of contact holes, and the surface geometry such as corners and edges of various features.

The requirement of small features with close spacing between adjacent features requires high resolution photolithographic processes. In general, lithography refers to processes for pattern transfer between various media. It is a technique used for integrated circuit fabrication in which a silicon slice, the wafer, is coated uniformly with radiation sensitive film, the resist, and an exposing source (such as optical light, x-rays, or an electron beam) illuminates selected areas of the surface through an intervening master template, the mask, for a particular patter. The lithographic coating is generally a radiation-sensitive coating suitable for receiving a projected image of the subject pattern. Once the image is projected, it is indelibly formed in the coating. The projected image may be either a negative or a positive image of the subject pattern. Exposure of the coating through a photomask causes the image area to become either more or less soluble (depending on the coating) in a particular solvent developer. The more soluble areas are removed in the developing process to leave the pattern image in the coating as less soluble polymer.

Present techniques in optical projection printing can resolve images of submicron when photoresists with good linewidth control are used. However, reflection of light from substrate/resist interfaces may produce variations in light intensity scattering of light in the resist during exposure, resulting in non-uniform photoresist linewidth development. Constructive and destructive interference resulting from reflected light is particularly significant when monochromatic or quasi-monochromatic light is used for photoresist exposure. In such cases, the reflected light interferes with the incident light to form standing waves within the resist. In the case of highly reflective substrate regions, the problem is exacerbated since large amplitude standing waves create thin layers of underexposed resist at the wave minima. The underexposed layers can prevent complete resist development causing edge acuity problems in the resist profile.

Antireflective coatings are known and used to mitigate the aforementioned problems. However, the antireflective coatings (ARC) layers are insufficient when used in connection with a Deep Ultra-Violet (DUV) photoresist due to acid formation in the resist when exposed. Therefore, when utilizing a DUV resist, the top portions of the ARC layer can be oxidized to mitigate footing of the patterned features after development of the resist layer. However, the thickness of the oxidized ARC layer is critical. Insufficient oxidation may result in problems with critical dimension control, which results in costly repair, fabrication delays and product yield losses. Therefore, there is an unmet need for a system and method for determining and controlling the appropriate oxidation of an ARC layer during a photoresist process.

SUMMARY OF THE INVENTION

The present invention relates to a system and method for providing in-situ thickness and process monitoring to help achieve a desired thickness of an oxidized ARC portion disposed over an ARC layer. The system and method may be employed to monitor the oxidized ARC portion during growth as well as during processing of the oxidized ARC layer. During semiconductor processing, a photoresist layer (e.g., DUV resist) may be deposited over the oxidized ARC layer for patterning. However, removal of the photoresist layer can damage the underlying oxidized ARC or ARC layer, resulting in diminished CD control and ultimately, poor device performance. Therefore, by monitoring the thickness of the oxidized portion of the ARC layer during semiconductor processing, one or more process control parameters may be adjusted to help achieve a desired oxidized portion thickness. As a result, the number of process steps required to achieve the desired oxidized portion thickness may be reduced, providing a more efficient and economical process.

Alternatively, the system and method according to the present invention may be employed in a closed-loop system with feedback control for optimizing ARC and oxidized ARC thickness while mitigating defective device formation and wafer yield loss. For example, the system and method may detect and assess the thickness of the ARC and/or oxidized ARC layer to determine an amount of oxidized ARC layer lost or damaged. The actual thickness may then be compared to a desired or preferred thickness. According to these measurements, the oxidized ARC layer may then undergo further processing to repair the current and/or subsequent wafer to mitigate recurring defects.

One aspect of the present invention provides a semiconductor processing system. The system includes a processing chamber operable to form an oxidized ARC layer or portion over an ARC layer on a substrate located in the chamber. An x-ray scattering/reflectometry system performs in-situ thickness measurements of the oxidized portion being formed and provides a measurement signal indicative of the measured thickness. In accordance with another aspect of the present invention, the thickness of the ARC layer may also be monitored and controlled. A signature is then generated utilizing the measurement signal and the signature is compared with a library of signatures to determine the thickness of the oxidized portion.

Yet another aspect of the present invention provides a method to facilitate formation of an oxidized portion of an ARC layer on a substrate. The method includes forming an oxidized portion of an ARC over an ARC layer disposed on the substrate. An x-ray beam is directed at the oxidized portion and a measurement signal is generated based-on the reflected (scattered) portion of the x-ray beam. The thickness of the oxidized portion is then determined based on the measurement signal while the oxidized portion is being formed at the substrate.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DISCLOSURE OF INVENTION

Figure 1:
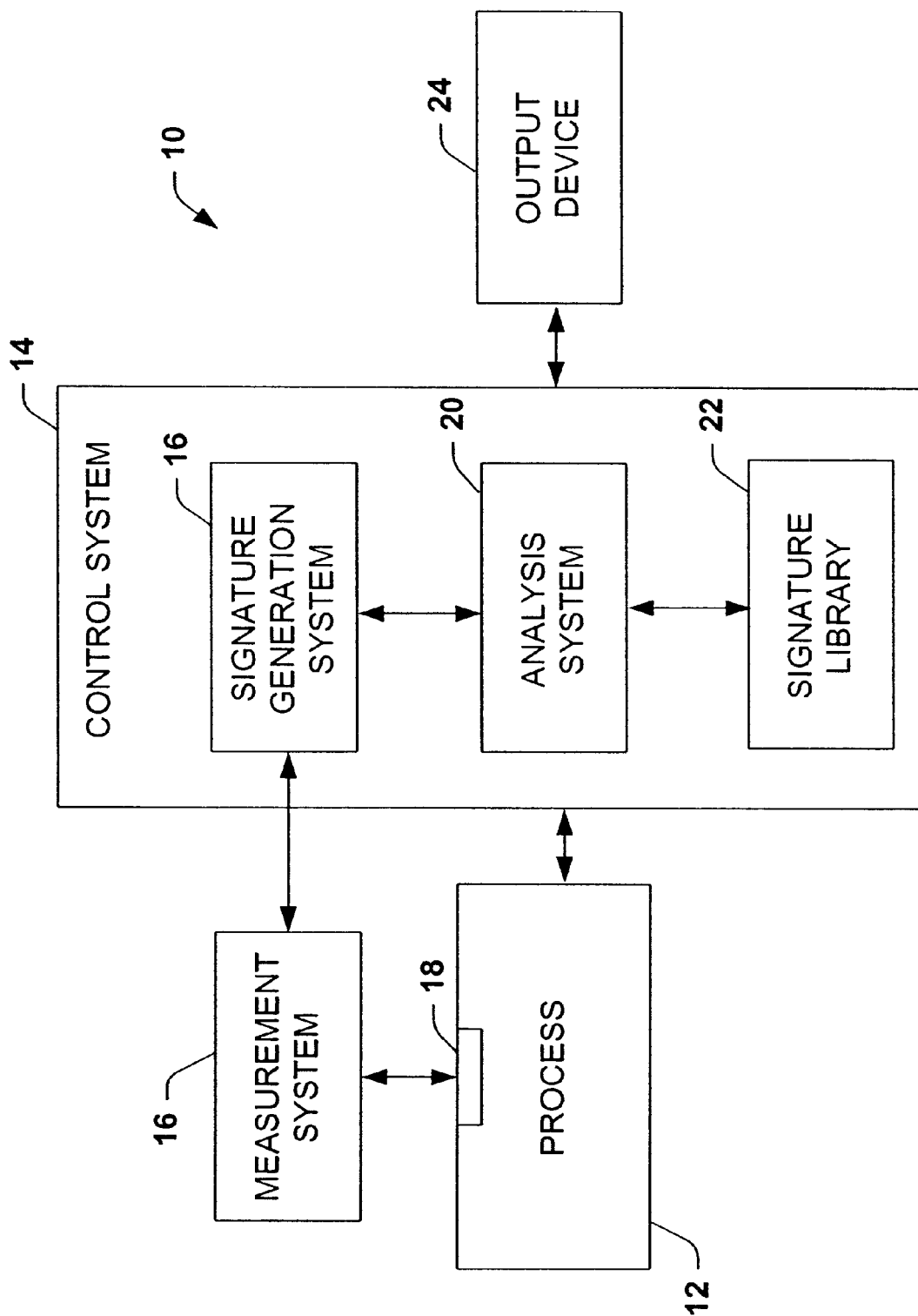
FIG. 1 illustrates a high-level block representation of a system in accordance with one aspect of the present invention.

The present invention involves a system and method for in-situ monitoring and control of an oxidation process associated with an ARC layer. One aspect of the invention relates to a system and method employing x-ray reflectometry to facilitate determining a thickness of an ARC layer and an oxidized portion of the ARC layer. The actual thickness may differ from the desired thickness as a result of insufficient or flawed oxidation or as a result of damage caused by the removal of an overlying photoresist film (e.g., DUV photoresist). Removal or stripping of photoresist films can be performed using a wet (e.g., diluted sulfuric acid solution) or plasma stripper. When the photoresist is stripped from an underlying oxidized ARC or ARC layer, damage to either or both layers may occur. The damage may be visualized by measuring the thickness of the layers.

Thus, the system and method mitigate footing problems associated with utilizing DUV photoresist films in patterning processes of a semiconductor substrate. The system and method employ a library of signatures which are stored in a memory. An x-ray beam is directed to the surface of an ARC, and the reflected beam is collected and analyzed. One or more signatures of the reflected x-ray beam can be generated and the one or more signatures are compared to the signatures of the library, so as to determine the approximate thickness of the ARC layer. The ARC layer is then oxidized and the process is repeated for the oxidized portion of the ARC. Alternatively, the thickness of the ARC layer can be determined after or during formation of the oxidized portion of the ARC layer.

The system and method can be employed in-situ, so that the thickness of either or both the ARC layer and the oxidized portion of the ARC layer can be monitored and controlled. Alternatively, the system and method may be employed in a closed-loop system with feedback control to optimize the thickness of the ARC and the oxidized ARC layers in order to mitigate defective oxidized ARC layer formation and to facilitate improved device performance. In the closed loop system, measured data relating to the thickness of the ARC and oxidized ARC layers may be fed back into the fabrication system for immediate system adjustments. Thus the system may be continuously optimized to achieve the desired ARC thicknesses and to account for wafer-to-wafer variations.

The present invention is to be described with reference to FIGS. 1–9 below, wherein like reference numerals are used to refer to like elements throughout. In the following description, for purposes of explanation, numerous specific details are set forth in order to provide a thorough understanding of the present invention. It may be evident, however, to one skilled in the art that the present invention may be practiced without these specific details. In other instances, well-known structures and devices are shown in block diagram form in order to facilitate description of the present invention.

Referring initially to FIG. 1, a system 10 for in-situ monitoring and/or determination of thickness measurements in connection with a process of forming an ARC layer and an oxidized portion of the ARC layer (schematically indicated at 12) is shown. The process 12, for example, includes thin film growth, etching, and/or thin film deposition of an ARC layer (e.g., SiON) on top of the layer to be patterned (e.g., polysilicon, oxide, metal). The process, for example, can include oxidation of the ARC layer by injection of oxygen into the process causing a top portion of the ARC layer to oxidize. Alternatively, an ARC material may be oxidized and grown or deposited on top of the ARC layer. The system 10 also includes a control system 14 for controlling operating characteristics of the process 12. The operating characteristics associated with the process 12 may include, for example, deposition and/or oxidation enablement, temperature, concentration of gases within the process, pressure associated with the process, and timing parameters associated with different steps in a multi-step fabrication process. The control system 14 may adjust one or more selected operating parameters of the process 12 based on sensed operating conditions associated with such process 12.

A measurement system 16 is operatively associated with the process 12 to measure in-situ thickness of the ARC layer and/or oxidized portion of the ARC layer as it is being formed. That is, the measurement system 16 includes a thickness monitoring portion 18, which may be located within or integrated into the process 12 and which may include an enclosed processing chamber. The measurement system 16, for example, samples the thickness of layers being formed on the substrate at one or more locations, such as near the center and near one or more edge locations of the substrate. In particular, it may be desirable to obtain measurements from two or more spaced-apart locations, such as the center and one or more edge positions. Such measurements may enable a better determination as to uniformity of the layer thickness, which in accordance with an aspect of the present invention, may be employed to adjust the fabrication process to achieve a desired level of uniformity of layer thickness.

The measurement system 16 may implement any known technique operable to measure the thickness of the thin film formed in the process 12. Examples of techniques that may be utilized in accordance with an aspect of the present invention include optical interference, x-ray reflectometry, capacitance and use of an associated color chart. Microprocessor-controlled optical interference is a common type of optical measurement technique that could be employed.

The measurement system 16 is coupled to the control system 14 for providing a signal indicative of the measured layer thickness being formed in the process 12. The control system 14, for example, includes a memory (not shown) for storing a target layer thickness, which may vary according to the process. The control system 14 also includes a signature generation system 16, which creates a signature from or based on the signal measurements over a pre-determined wavelength range and/or angle of incidence. The control system 14 also includes a signature library 22 that includes hundreds of thousands of signatures, each corresponding to a particular type and thickness of ARC and/or oxidized ARC layers.

An analysis system 20 is provided for comparing the generated signature with signatures in the signature library 22. By examining a signature library 22 of intensity/angle signatures, a determination can be made concerning the properties of the surface, such as thickness of the layer being formed thereon. The control system 14 is coupled to the process 12 and maybe programmed and/or configured to compare the measured thickness relative to the target thickness and determine what action, if any, should be taken to drive the process 12 so that a target thickness and/or a desired level of uniformity of thickness may be achieved. The control system 14 is also coupled to an output device 24 which may be used to display results to a user.

The system 10 further may include one or more process sensors (not shown) for monitoring process operating conditions and providing an indication of such conditions to the control system 14. Thus, the control system 14 is able to adjust process operating conditions based on the measured thickness (e.g., based on a signal/generated signature from the measurement system 16) and the sensed process operating conditions (e.g., based on a signal from the other process sensors). In this way, the control system 14 may selectively refine the ARC formation and oxidation process 12 to accommodate variations in sensed process conditions and measured layer thickness at various stages of the layer formation process. For example, the control system 14 may adjust gas flow rates, pressure, temperature, thermal oxidation time and/or layer formation time (e.g., deposition time or layer growth time) based on the conditions monitored by the measurement system 16 and the one or more sensors. As a result, the system 10 is capable of achieving a more precise and/or uniform film thickness in order to refine the process without an increase in process steps.

Figure 2:
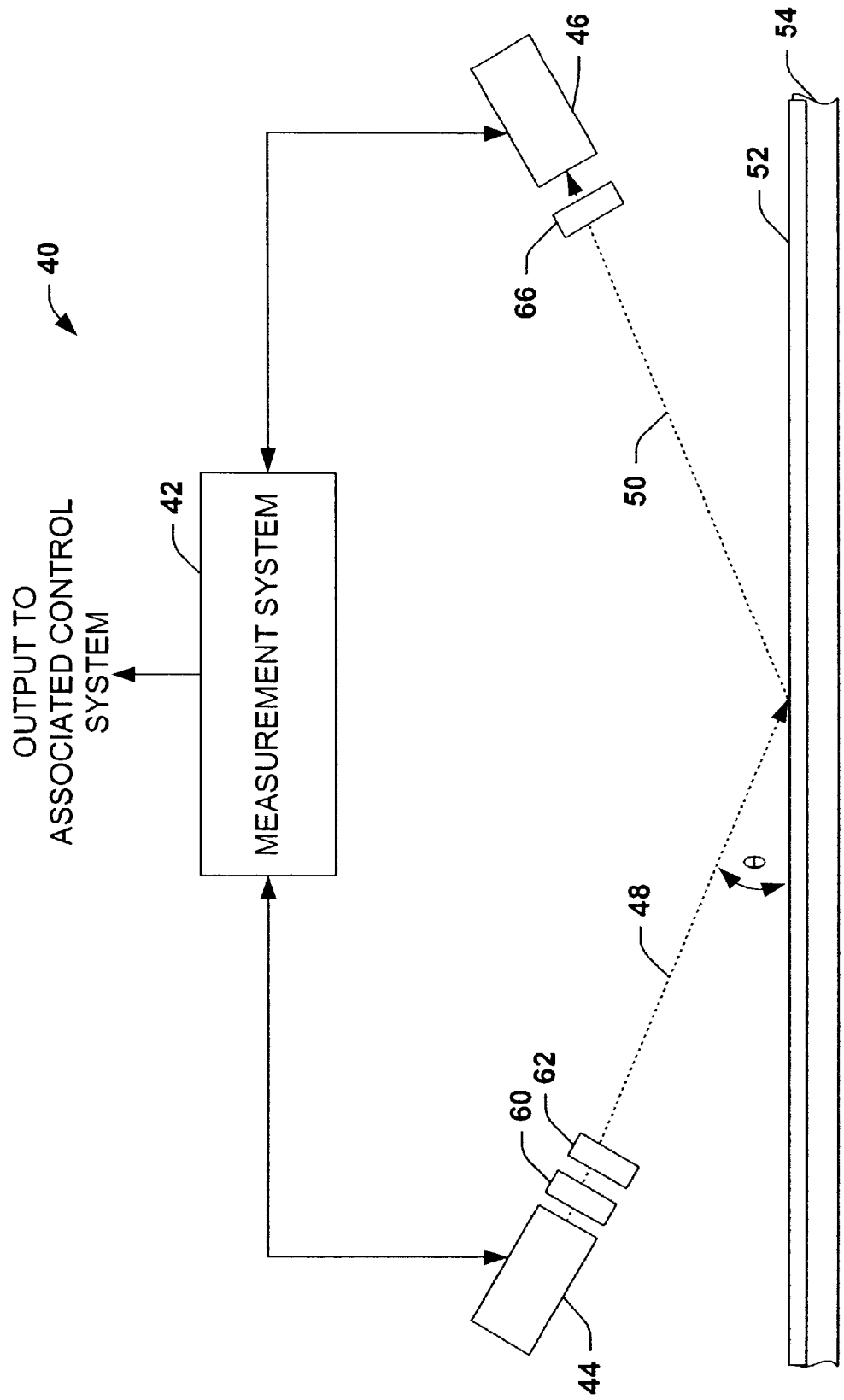
FIG. 2 illustrates a high-level block diagram illustrating an example of a measurement system employing x-ray reflectometry that may be utilized in accordance with one aspect of the present invention.

Also included in the system 10 is an x-ray reflectometry system (FIG. 2). X-ray reflectometry may be employed to monitor and control the ARC layer and the oxidized ARC layer thickness. X-ray reflectometry is a non-destructive optical technique, which deals with the measurement and interpretation state of x-rays scattering from a sample surface boundary. When x-rays strike a surface at glancing incidence, they can reflect (scatter) off the surface. However, if the surface is rough or covered by a film, then the x-ray reflectivity of a surface can change. X-ray reflectometry (XRR) takes advantage of this effect by measuring the intensity of X-rays reflected from a surface as a function of an incident angle. For example, thin films on a surface may give rise to oscillations of the x-ray intensity as a function of the incident angle.

In addition, the characteristic scattering of x-rays from atoms may also be done in lattices, referred to as Bragg scattering and exemplified by the formula $n\lambda=2d\sin\theta$, where n is an integer, $\lambda$ is the x-ray wavelength, d is the spacing between layers (analogous to layer thickness or depth), and $\theta$ (theta) is often referred to as the Bragg angle or incident angle. Bragg scattering gives information about type and changes in a crystal lattice. Scattering x-ray radiation from thin films is somewhat analogous to scattering radiation at plane parallel plates. However, in the latter case, special care must be taken since the refractive index for all materials is close to 1, and total reflection occurs for incident angles smaller than the critical angle. Total reflection may also occur because when dealing with x-rays, it is important to note that any material is optically thinner than air. Oscillations of x-ray intensity are only visible in a small range around the critical angle $\theta_c$ (see FIG. 5). Furthermore, the critical angle of total reflection is small, such as for example, $\sim 0.2°-1°$ for a wavelength $\lambda$ of $\sim 0.1$ nm.

FIG. 2 illustrates an example of an x-ray reflectometry system 40 that may be implemented in accordance with the present invention to measure the thickness of an oxidized portion 52 as it is formed on an ARC layer 54. The x-ray reflectometry system 40 includes a measurement system 42 coupled to a light source 44 and a detector 46. The light source 44 may be an x-ray tube of polychromatic x-ray radiation. Light beam 48 from the light source 44 travels through a collimator 60 and a crystal monochromator 62, which is located between the light source 44 and a sample holder (not shown). To switch the measurement to a new spectral region, it is necessary to rotate the monochromator 62 as well as other elements of this system 40 corresponding to a new Bragg angle.

At least a portion of the x-ray beam is reflected, indicated at 50, and received at the detector 46. The detector 46 measures the intensity of the different wavelengths of light through the wavelength range of interest that pass through an analyzer 66. The analyzer 66 serves to maintain the reflected beams 50 incident upon it with their corresponding spectral region so that the detector 46 can characterize them. The detector 46 or the measurement system 42 may then determine x-ray reflectivity intensity as a function of an incident angle, referred to as $\theta$. One or more signatures are thus generated corresponding to the scattering angle and x-ray reflectivity. Hence the generated signature corresponds to the thickness of the oxidized portion 52 of the ARC layer 54 and/or the thickness of the ARC layer 54.

Figure 5:
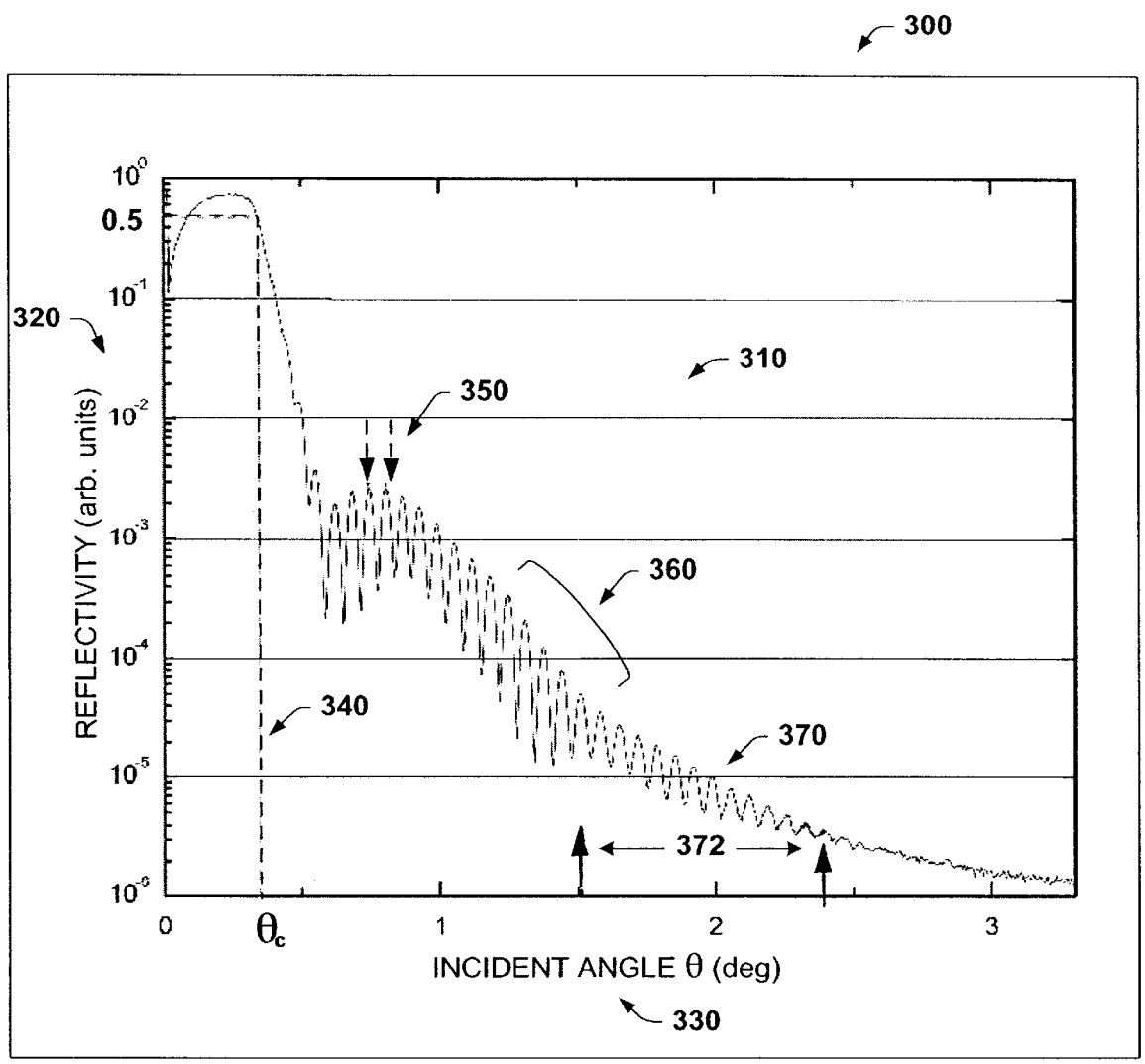
FIG. 5 illustrates a graph of exemplary x-ray reflectometry data corresponding to the thickness of an ARC layer in accordance with one aspect of the present invention.

According to another aspect of the invention, surface roughness $\sigma_{rms}$ of an oxidized portion of an ARC layer may be determined using x-ray reflectometry. However, measuring roughness differs slightly from measuring thickness. Surface roughness may be calculated by the formula: $R_F^{rough}=R_F \exp(-K_Z^2 \sigma_{rms}^2)$, where $R_F$ is the reflected intensity and $|K_Z|=2\pi\sin\theta/\lambda$. The system 10 (FIG. 1), together with the x-ray reflectometry system 40 (FIG. 2) may be employed as described above to determine surface roughness. However, to obtain vertical surface and interface roughness measurements, the x-ray scattering vector (incident angle) must be perpendicular to the surface. On an x-ray reflectivity spectrum, such as shown in FIG. 5 below, surface roughness may be indicated by a drop in reflectivity (intensity).

Figure 3:
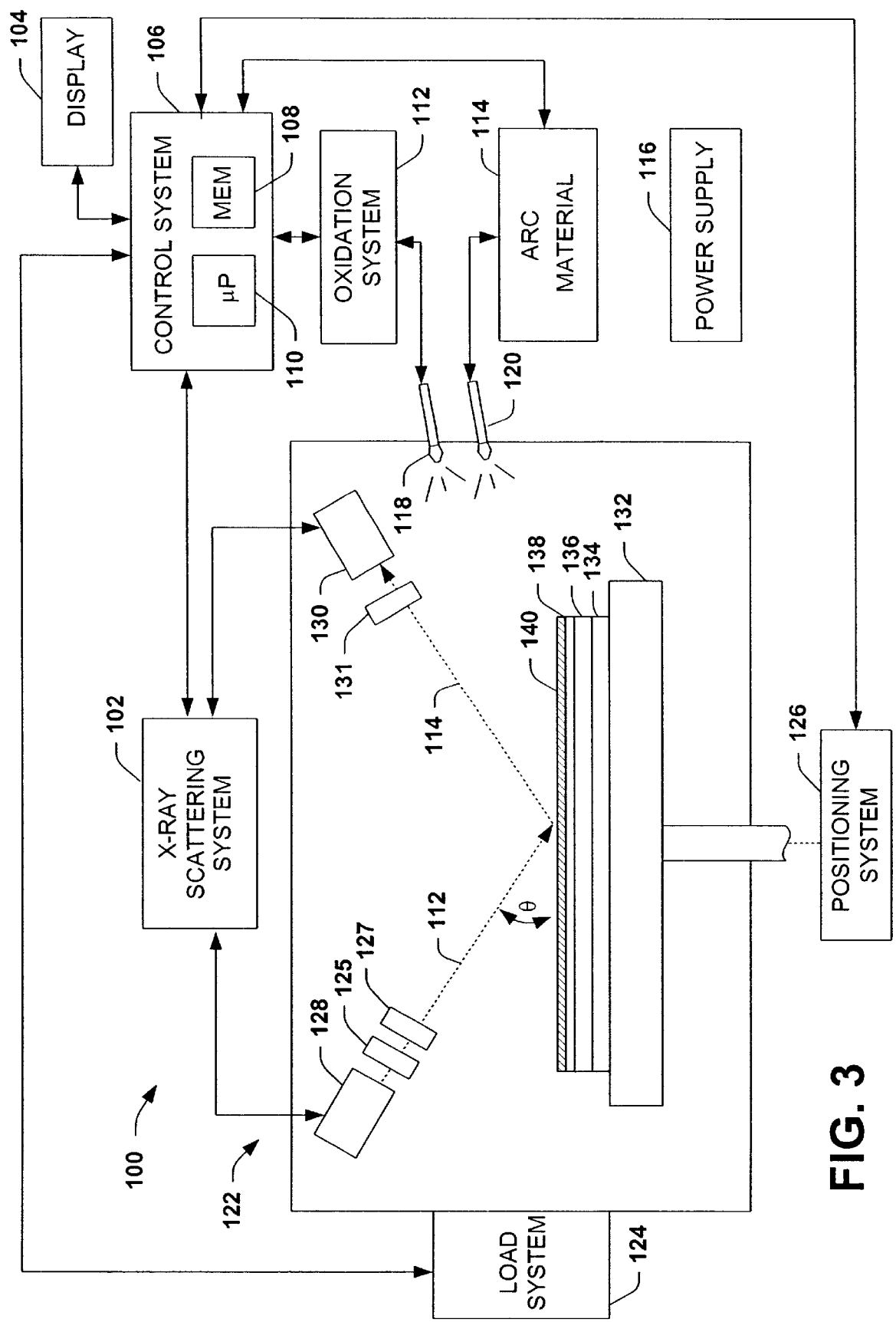
FIG. 3 illustrates a functional block diagram of a system in accordance with one aspect of the present invention.
Figure 4:
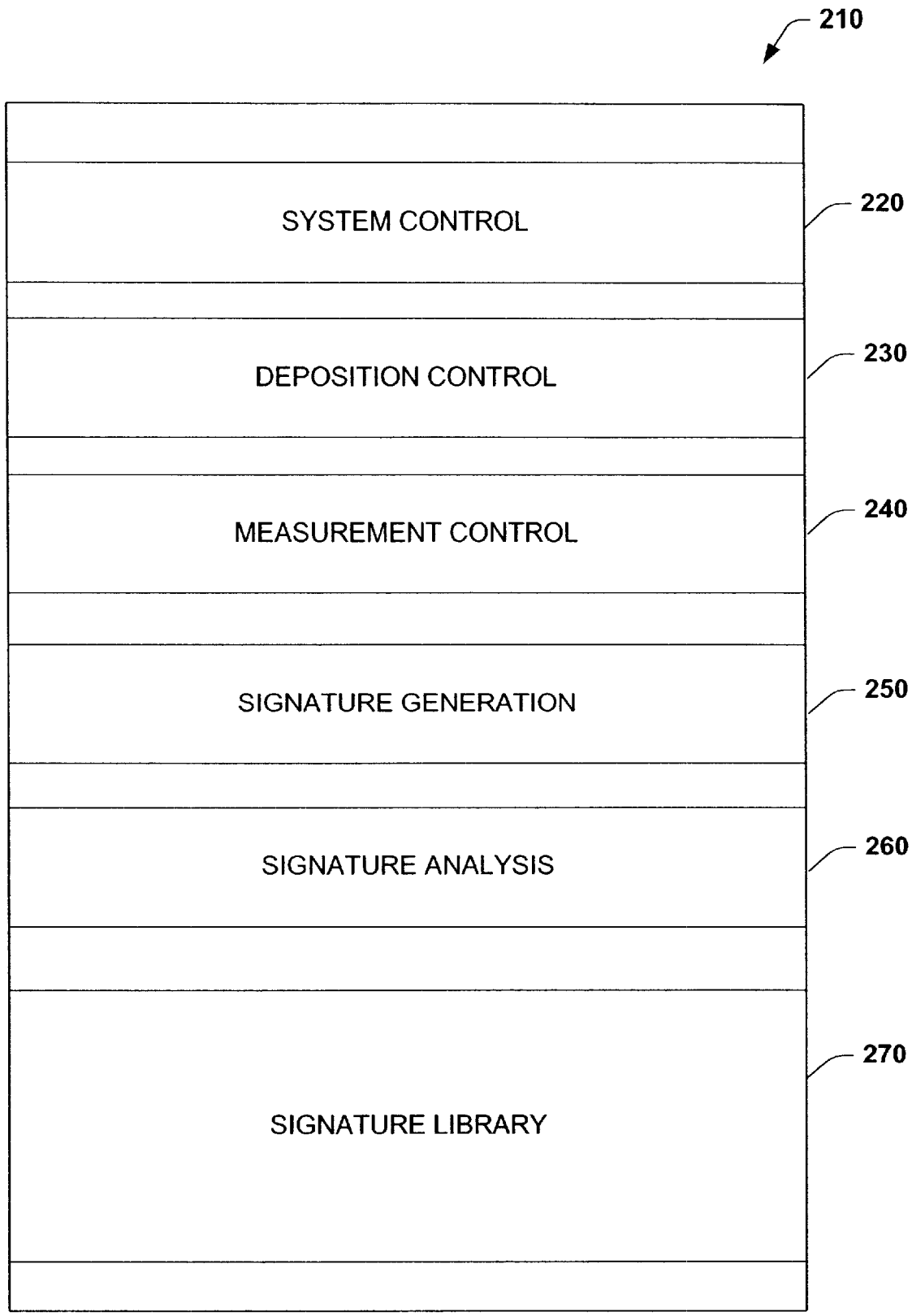
FIG. 4 illustrates a block diagram of program modules that reside in a memory system in accordance with one aspect of the present invention.

FIGS. 3–4 illustrate examples of a system for employing x-ray reflectometry techniques to determine the thickness of an oxidized portion of an ARC layer. FIG. 3 illustrates a system 100 having an x-ray scattering system 102 for in-situ layer thickness monitoring in accordance with one aspect of the present invention. In this example, the system 100 forms an ARC layer 138 by chemical vapor deposition (CVD). The ARC layer 138 is formed over an insulating layer 136 disposed over a substrate 134. Examples of CVD processes that may be utilized, in accordance with an aspect of the present invention, include Low Pressure CVD (LPCVD), Plasma Enhanced CVD (PECVD), and Rapid Thermal CVD (RTCVD). It is to be appreciated, however, that the present invention is applicable to other types of thin film formation, such as other deposition techniques (e.g., Physical Vapor Deposition (PVD), Metal Organic Chemical Vapor Deposition (MOCVD), Pulsed Laser Deposition (PLD)) and film growth techniques.

The system 100 includes a process chamber 122 that includes a support, such as a stage 132 (or chuck) operative to support the substrate 134, such as a wafer. A positioning system 126 is operatively connected to the support 132 for positioning the stage 132 at a desired position within the chamber 122. It is to be appreciated that wafer positioning systems are rapidly evolving and that any such system may be employed in accordance with an aspect of the present invention.

An ARC material layer gas distribution system 114 is operably coupled to the chamber 122 for selectively providing gaseous chemicals into the chamber to form the ARC film layer 138 on the substrate 134. By way of illustration, the gas distribution system 114 includes a source of a gaseous medium (a vapor) of ARC material (e.g., silicon oxynitride) to be formed on the substrate. The gas is provided into the chamber through a conduit that terminates in a nozzle, indicated at 120. While, for purposes of brevity, a single nozzle 120 is shown in FIG. 4, it is to be appreciated that more than one nozzle or other gas delivery mechanisms may be utilized to provide gas into the chamber 122 for film formation in accordance with an aspect of the present invention.

An oxidation system 112 also is provided for controlling the injection of oxygen into the processing chamber 122. The oxidation system 112 is adapted to inject oxygen into the chamber 122 to oxidize the ARC layer 138 and form the oxidized ARC portion 140. By way of illustration, the oxidation system 112 includes a source of oxygen to be injected into the chamber 122. The oxygen is provided into the chamber through a conduit that terminates in a nozzle, indicated at 118. Although, a single nozzle 118 is shown in FIG. 3, it is to be appreciated that more than one nozzle or other oxygen delivery mechanisms may be utilized to provide oxygen into the chamber 122 for oxidation of the top portion of the ARC layer 138 in accordance with an aspect of the present invention.

The system 100 also may include a load system 124 operatively connected to the chamber 122 for loading and unloading substrates (e.g., wafers) into and out of the processing chamber. The load system 124 typically is automated to load and unload the wafers into the chamber at a controlled rate. The x-ray scattering system 102 is operative to measure film thickness in-situ, in accordance with an aspect of the present invention. In the example illustrated in FIG. 3, the x-ray scattering system 102 is operative to measure the thickness of the ARC layer 138 in addition to the thickness of the oxidized portion 140 of the ARC layer 138.

The x-ray scattering system 102 includes a polychromatic light source 128, a collimator 125, a monochromator 127, an analyzer 131 and a detector 130. Alternatively, the x-ray scattering system 102 may have a cutting slit, a Göbel mirror, an antiscatter slit and a detector slit (all not shown). The x-ray scattering system 102 operates in the same manner as the x-ray reflectometry system 40 described in FIG. 2. The polychromatic light source 128 provides a light beam 112 toward an exposed surface of the substrate 134 at which the layer is being formed. The beam 112 interacts with the surface and layer(s) and is reflected. The reflected beam(s) 114, which is received at the detector portion of the source/detector 130, has beam properties (e.g., magnitude and/or phase), which may be employed to determine an indication of layer thickness. A plurality of incident beams from one or more sources also may be directed at different spaced apart locations of the substrate to obtain corresponding measurements of layer thickness substantially concurrently during the fabrication process. The concurrent measurements, in turn, provide an indication of the uniformity of layer thickness across the substrate. By way of illustration, the intensity of light over a selected wavelength and range of incident angles varies as a function of layer thickness in x-ray reflectometry.

The x-ray scattering system 102 provides information indicative of the measured properties to a control system 106. Such information may be the raw phase and intensity information. Alternatively or additionally, the x-ray scattering system 102 may be designed to derive an indication of layer thickness based on the measured optical properties and provide the control system 106 with a signal indicative of the measured layer thickness according to the detected optical properties. The scattering (incident) angle and intensity of the reflected light can be measured and plotted in a spectrum.

In order to determine layer thickness, for example, measured signal characteristics may be employed to generate a signature corresponding to the reflectivity intensity over the angle θ range. The generated signatures may be compared with a signal (signature) library of known signatures of the same to determine the thickness of the ARC layer 138 and/or the thickness of the oxidized portion 140 of the ARC layer. Such substantially unique x-ray reflectivity intensity signatures are produced by light reflected from and/or refracted by different surfaces due, at least in part, to the complex index of refraction of the surface onto which the light is directed.

The signature library can be constructed from observed intensity/angle signatures and/or signatures generated by modeling and simulation. By way of illustration, when exposed to a first incident light of known intensity, wavelength and angle, a first feature on a wafer can generate a first component of an intensity/angle signature. Similarly, when exposed to the first incident light of known intensity, wavelength and angle, a second feature on a wafer can generate a second component of a intensity/angle signature. The components can be determined over a pre-determined range of incident angles and aggregated to form a signature. For example, a particular type of thin film having a first thickness may generate a first signature while the same type of film having a different thickness may generate a second signature, which is different from the first signature.

Observed signatures can be combined with simulated and modeled signatures to form the signature library. Simulation and modeling can be employed to produce signatures against which measured intensity/angle signatures can be matched. In one exemplary aspect of the present invention, simulation, modeling and observed signatures are stored in a signature library containing, for example, over three hundred thousand angle/intensity signatures. Thus, when the intensity/angle signals are received from x-ray scattering detecting components, the intensity/angle signals can be pattern matched, for example, to the library of signatures to determine whether the signals correspond to a stored signature. Interpolation between the two closest matching signatures further may be employed to discern a more accurate indication of thickness from the signatures in the signature library. Alternatively, artificial intelligence techniques may be employed to calculate desired parameters of the wafer under test based on the detected optical properties.

The control system 106 includes a processor 110, such as a microprocessor or CPU, coupled to a memory 108. The processor 110 receives measured data from the x-ray scattering system 102. The processor 110 also is operatively coupled to the ARC material gas distribution system 114, the oxidation system 112, the positioning system 126 and the load station 124. The control system 106 is programmed/and or configured to control and operate the various components within the processing system 100 in order to carry out the various functions described herein.

The processor 110 may be any of a plurality of processors, such as the AMD K6®, ATHLON™ or other similar processors. The manner in which the processor 110 can be programmed to carry out the functions relating to the present invention will be readily apparent to those having ordinary skill in the art based on the description provided herein.

The memory 108 serves to store program code executed by the processor 110 for carrying out operating functions of the system as described herein. The memory 108 may include read only memory (ROM) and random access memory (RAM). The ROM contains among other code the Basic Input-Output System (BIOS) which controls the basic hardware operations of the system 100. The RAM is the main memory into which the operating system and application programs are loaded. The memory 108 also serves as a storage medium for temporarily storing information such as temperature, temperature tables, position coordinate tables, interferometry information, thickness tables, and algorithms that may be employed in carrying out the present invention. The memory 108 also can hold patterns against which observed data can be compared as well as information concerning grating sizes, grating shapes, x-ray reflectivity/ scattering information, achieved profiles, desired profiles and other data that may be employed in carrying out the present invention. For mass data storage, the memory 108 may include a hard disk drive.

A power supply 116 provides operating power to the system 100. Any suitable power supply (e.g., battery, line power) may be employed to carry out the present invention. The system further may include a display 104 operatively coupled to the control system 106 for displaying a representation (e.g., graphical and/or text) of one or more process conditions, such as layer thickness, temperature, gas flow rates, etc. The display 104 further may show a graphical and/or textual representation of the measured optical properties (e.g., refraction index and absorption constant) at various locations along the surface of the substrate.

As a result, the system 100 provides for monitoring process conditions, including layer thickness and other sensed process-related conditions, associated with the layer formation process within the chamber 122. The monitored conditions provide data based on which the control system 106 may implement feedback process control in a closed loop so as to form a layer having a desired thickness, such as a uniform thickness across the substrate.

FIG. 4 illustrates a plurality of program modules that can reside in a memory 210 employed in the systems illustrated in FIG. 3. The memory 210 includes a system control module 220 for controlling the initialization of components in the system, the load system, the positioning system and rotation of the chuck. The system control module 220 also operates as a kernel for providing a central communication mechanism between the other modules in the memory 210. A deposition control module 230 provides control for enabling and disabling the ARC material gas distribution system and the oxidation system or the oxidized ARC material gas distribution system. The measurement control module 240 initializes and controls the x-ray reflectometry system for operating the polychromatic light source, rotation of the monochromator or analyzer and sampling of the detector. A signature generation module 250 aggregates the raw signal samples from the x-ray reflectometry system and provides an actual measured signature of the thickness of the oxidized ARC material layer and/or ARC material layer. The signature analysis module 260 searches a signature library 270 and compares the actual measured signature(s) with stored signatures in the signature library 270.

Once a match of the signatures is determined, a corresponding thickness is determined and passed back to the system control module 220. The system control module 220 then determines if the optimal thickness has been achieved. If the optimal thickness has been achieved, the system control module 220 notifies the deposition control module 230 to terminate deposition of the material or oxidation of the material.

Turning now to FIG. 5, an exemplary spectrum 300 showing data 310 characteristic of the x-ray reflectometry system 102 is illustrated. The data 310 corresponds to a multi-layer structure such as, for example, an oxidized ARC layer over an ARC layer formed on a substrate. The spectrum 300 represents reflectivity 320 (x-ray intensity) as a function of an incident angle $\theta$ 330. The data 310 associated with the spectrum 300 is with respect to the critical angle 340 having a 0.5 reflectivity and the wavelength $\lambda$ being about 0.10 nm.

Interference patterns 360 from thin films are only visible in a small range about the critical angle. Thus, as shown in the spectrum 300, the interference pattern 360 is observed in a small range from the critical angle 340. According to x-ray reflectometry theory, the film thickness 350 for a thin layer such as an ARC layer (over a substrate) can be determined by the formula: $d \cong \lambda/(2\Delta\theta)$, where d is the layer thickness, ) $\lambda$ is the x-ray wavelength, and $\Delta\theta$ is the change in angle. A thin film layer (on a substrate) will produce oscillations 350 in the reflectivity related to the layer's thickness known as Kiessig fringes 350. As can be seen by the spectrum 300 at oscillations 350, there is little or no change in the angle $\theta$ (at dashed arrows). Therefore, according to the formula, the thickness d will be relatively larger than for the layer represented by 360. In addition, rapid oscillations correspond to a relatively thick layer and wider oscillations correspond to a thinner layer. Thus, the relatively rapid oscillations 350 in the spectrum 300 support the above conclusion.

An interference pattern (beat) is created when more than one layer is present, as schematically indicated by 360. That is, the interference pattern represents the thickness of a layer formed over another layer on a substrate. Here, the interference pattern 360 indicates-the thickness of a second layer such as oxidized ARC layer. As can be seen by the interference pattern or beat 360, the change in angle $\Delta\theta$ is greater than at the oscillations 350. This means that the oxidized ARC layer is thinner than the ARC layer. More precise thickness measurements may be ascertained by using the formula $d \cong \lambda/(2\Delta\theta)$ as stated above.

In addition to information provided by the oscillations 350 and interference pattern 360, a drop in intensity (reflectivity), indicated at 370 and by the θ range 372, illustrates an amount of surface roughness. Information related to the surface roughness of a layer may indicate planarization requirements and/or deficiencies.

Figure 6:
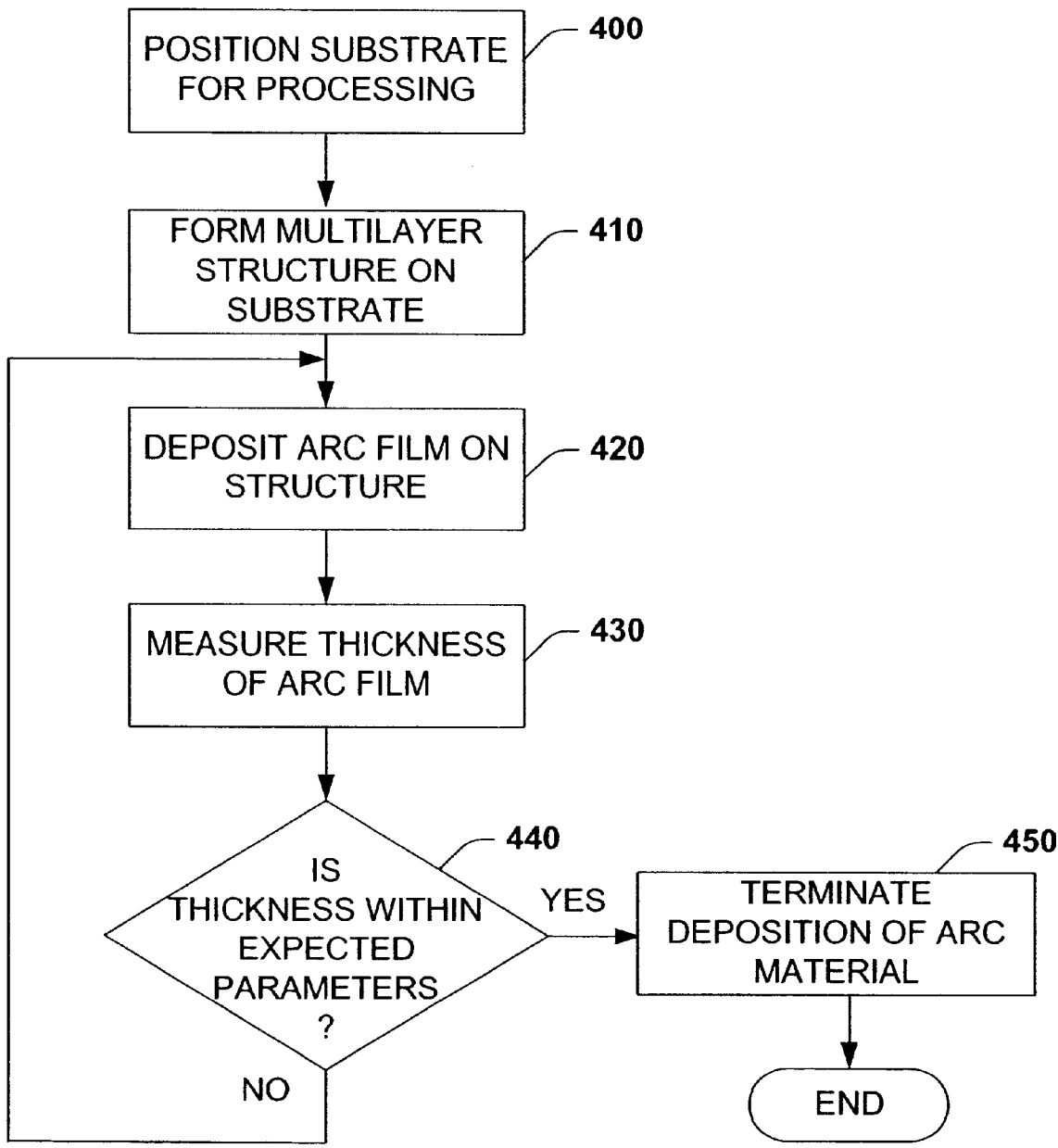
FIG. 6 illustrates a flow diagram illustrating a methodology for measuring a thickness of an ARC layer in accordance with one aspect of the present invention.
Figure 7:
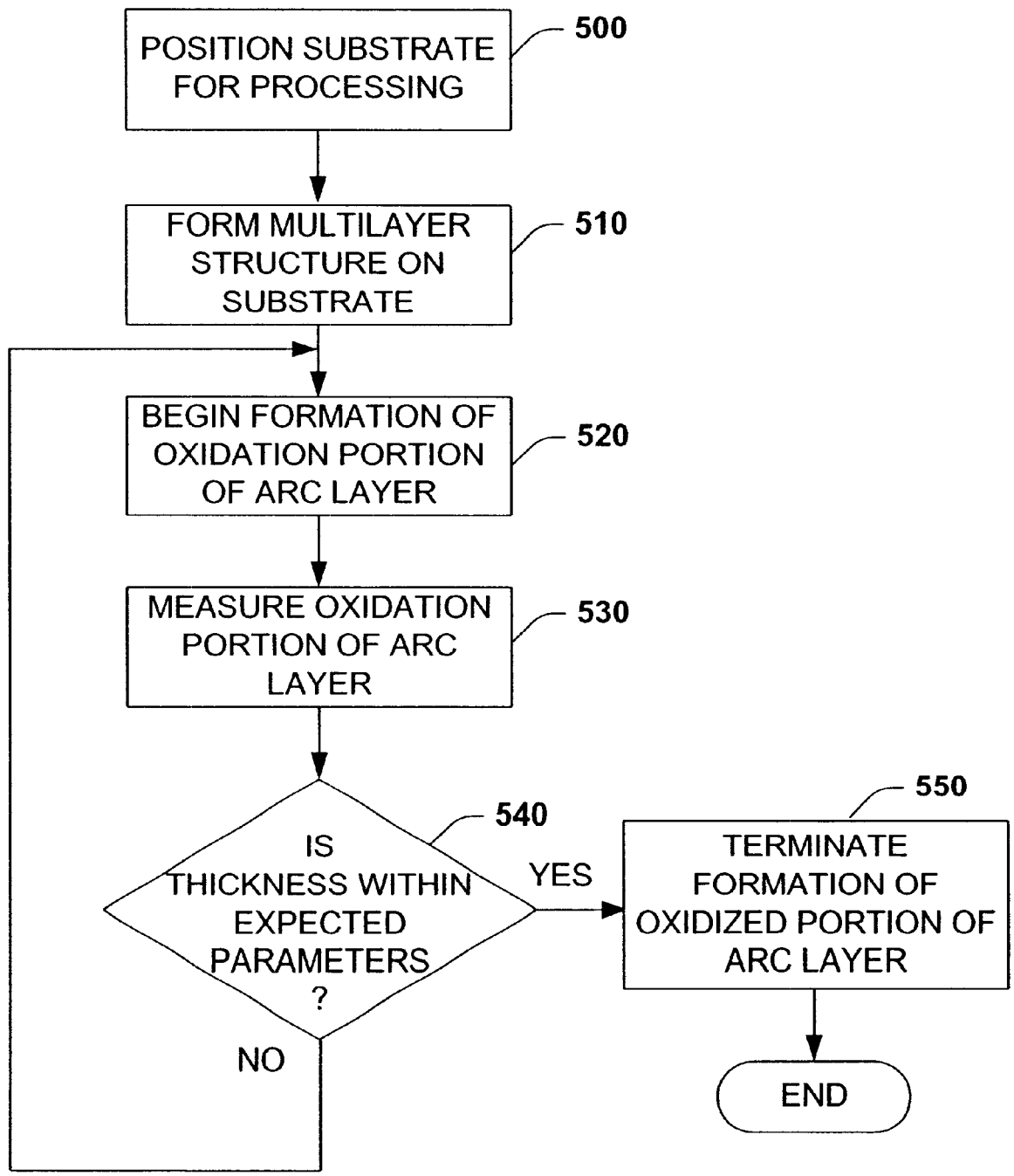
FIG. 7 illustrates a flow diagram illustrating a methodology for measuring a thickness of an oxidized portion of an ARC layer in accordance with one aspect of the present invention.

In view of the exemplary systems shown and described above, a methodology, which may be implemented in accordance with the present invention, will be better appreciated with reference to the flow diagrams of FIGS. 6 and 7. While, for purposes of simplicity of explanation, the methodologies of FIGS. 6 and 7 are shown and described as executing serially, it is to be understood and appreciated that the present invention is not limited by the illustrated order, as some blocks may, in accordance with the present invention, occur in different orders and/or concurrently with other blocks from that shown and described herein. Moreover, not all illustrated blocks may be required to implement a methodology in accordance with the present invention.

Turning now to FIG. 6, the methodology begins at 400 in which a substrate is positioned within an appropriate environment for desired processing. In this example, the processing is to include formation of an ARC film layer over a multi-layer structure, such as, for example, a silicon oxynitride (SiON) ARC layer formed over a polysilicon layer over an oxide layer over a silicon substrate.

After the substrate is positioned, the process proceeds to 410 in which a multi-layer structure is formed on the substrate. At 420, deposition of the ARC layer over the multi-layer structure begins. As mentioned above, ARC layer film formation may occur on a substrate, such as wafer, through a known deposition or film growth technique. The process then proceeds to 430.

At 430, the thickness of the thin layer being formed is measured. By way of example, the layer thickness is measured in-situ by a x-ray reflectometry system, although other non-destructive thickness measuring techniques also could be utilized in accordance with the present invention.

From 430, the process proceeds to 440 in which a determination is made as to whether the measured thickness is within expected operating parameters. This determination, for example, may include a comparison of the measured thickness with an expected (or target) value, such as may be derived based on previous processes, calculations using monitored operating conditions within the processing chambers, and/or a combination thereof. For example, a signal signature indicative of reflected and/or refracted light may be compared relative to a signature library to provide an indication of the thickness based on its intensity and/or phase of the reflected and/or refracted light. If the thickness is within expected operating parameters, the process proceeds to 450. At 450, the process terminates the deposition of the ARC material. If the thickness is not within expected operating parameters, the process returns to 420 and continues the deposition process.

FIG. 7 is another example of a flow diagram illustrating a methodology that may be employed, in accordance with an aspect of the present invention, to help form an oxidized portion of the ARC film layer having a desired thickness. The methodology begins at 500 in which a substrate is positioned within an appropriate environment for desired processing. In this example, the processing is to include formation of an oxidized portion of an ARC film layer over an ARC film layer over a multi-layer structure, such as, for example, an oxidized silicon oxynitride layer over a silicon oxynitride (SiON) ARC layer formed over a polysilicon layer over an oxide layer over a silicon substrate.

After the substrate is positioned, the process proceeds to 510 in which a multi-layer structure is formed on the substrate including deposition of an ARC layer over the multi-layer structure. As mentioned above, ARC layer film formation may occur on a substrate, such as wafer, through a known deposition or film growth technique. The process then proceeds to 520.

At 520, formation of the oxidized portion of the ARC layer begins. The oxidized layer may be formed by injecting oxygen into a process chamber in which the substrate resides as discussed with respect to FIG. 3. At 530, the thickness of the oxidized portion of the ARC layer being formed is measured. By way of example, the film thickness is measured in-situ by a x-ray reflectometry system, although other non-destructive thickness measuring techniques also could be utilized in accordance with the present invention.

From 530, the process proceeds to 540 in which a determination is made as to whether the measured thickness is within expected operating parameters. This determination, for example, may include a comparison of the measured thickness with an expected (or target) value, such as may be derived based on previous processes, calculations using monitored operating conditions within the processing chambers, and/or a combination thereof. For example, a signal signature indicative of reflected and/or refracted light may be compared relative to a signature library to provide an indication of the thickness based on its magnitude and/or phase of the reflected and/or refracted light. If the thickness is within expected operating parameters, the process proceeds to 550. At 550, the process terminates the formation of the oxidation portion of the ARC layer. If the thickness is not within expected operating parameters, the process returns to 520 and continues the formation of the oxidized portion of the ARC layer.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means")used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A semiconductor processing system, comprising:
   a processing chamber operable to selectively oxidize a portion of an anti-reflective layer over an anti-reflective layer formed on a substrate located in the chamber;
   an x-ray scattering measurement system for in-situ measuring a thickness of the oxidized portion being formed and for providing a measurement signal indicative of the measured thickness; and
   a control system for controlling operating characteristics of the formation environment within the chamber, the control system adjusting the operating characteristics to control formation of the oxidized portion based on the measurement signal.

2. The system of claim 1, further comprising an oxidation system adapted to inject oxygen into the chamber and oxidized a top portion of the anti-reflective layer to form the oxidized portion of the anti-reflective layer, the oxidation system being controlled by the control system.

3. The system of claim 1, further comprising an oxidized anti-reflective material distribution system operable to deposit oxidized anti-reflective material onto the anti-reflective material layer to form the oxidized portion, the oxidized anti-reflective material distribution system being controlled by the control system.

4. The system of claim 1, wherein the measurement system is an x-ray reflectometry system.

5. The system of claim 4, wherein the x-ray reflectometry system includes a polychromatic x-ray light source for generating a spectrum of incident angles at the oxidized portion and a detector to measure an intensity of reflected x-rays as a function of the incident angles.

6. The system of claim 5, the detector transmitting the measured intensity of the reflected x-rays with respect to the incident angles to a control system, the control system being further adapted to generate a signature of the reflected spectrum of the angles that corresponds to the thickness of the oxidized portion.

7. The system of claim 6, further comprising a library of signatures corresponding to various thicknesses of the oxidized portion, the control system being adapted to search the library for a match to the generated signature to determine a thickness of the oxidized portion.

8. The system of claim 7, wherein the control system controls a formation time period during which the oxidized portion is formed, the control system controlling the formation time period based on the determined thickness.

9. The system of claim 6, the control system generating a reflectivity signature component and an incident angle component corresponding to the oxide portion thickness.

10. The system of claim 6, further including a display operatively coupled to the control system and operative to display a visual representation of the measured thickness of the oxidized portion during fabrication.

11. The system of claim 1, the anti-reflective layer being formed of SiON and the oxidized portion being formed of oxidized SiON.

12. The system of claim 1, the oxidized portion mitigating footing problems associated with utilizing deep ultraviolet (DUV) resist.

13. A method to facilitate formation of an oxide portion of an anti-reflective layer on a substrate using a semiconductor processing system, comprising:

forming an oxidized portion of an anti-reflective coating over an anti-reflective layer disposed on the substrate;

reflecting a beam of x-ray radiation at the oxidized portion;

generating a measurement signal based on the reflected portion of the light beam; and determining a thickness of the oxidized portion based on the measurement signal while the oxidized portion is being formed at the substrate, the semiconductor processing system comprising:

a processing chamber operable to selectively oxidize a portion of an anti-reflective layer over an anti-reflective layer formed on a substrate located in the chamber;

an x-ray scattering measurement system for in-situ measuring a thickness of the oxidized portion being formed and for providing a measurement signal indicative of the measured thickness; and a control system for controlling operating characteristics of the formation environment within the chamber, the control system adjusting the operating characteristics to control formation of the oxidized portion based on the measurement signal.

14. The method of claim of 13, further comprising adjusting operating characteristics of formation of the oxidized portion to control formation of the oxidized portion as a function of the determined thickness.

15. The method of claim 13, further comprising generating a signature corresponding to the measurement signal.

16. The method of claim 15, further comprising comparing the generated signature with a library of signatures to determine the thickness of the oxidized portion.

17. The method of claim 16, the generated signature and the library of signatures having a reflectivity signature component and angle component corresponding to the oxide portion thickness.

18. The method of claim 17, further comprising controlling a formation time period based on the determined thickness.

19. The method of claim 13, the anti-reflective layer being formed of SiON and the oxidized portion being formed of oxidized SiON.

* * * * *